United States Patent [19]

Morris et al.

[11] Patent Number: 4,902,507
[45] Date of Patent: Feb. 20, 1990

[54] **TOXIC STRAINS OF THE BACTERIUM *BACILLUS THURINGIENSIS* FOR CONTROL OF THE BERTHA ARMYWORM *MAMESTRA CONFIGURATA***

[75] Inventors: Oswald N. Morris; Marc R. Trottier, both of Manitoba, Canada

[73] Assignee: Canadian Patents & Development Ltd., Ottawa, Canada

[21] Appl. No.: 85,172

[22] Filed: Aug. 14, 1987

[51] Int. Cl.[4] ........................ A01N 63/00; C12N 1/20; C12R 1/07

[52] U.S. Cl. ........................................ 424/93; 424/88; 424/92; 435/252.31

[58] Field of Search .............. 424/92898, 93; 435/253, 435/252.31

[56] References Cited

U.S. PATENT DOCUMENTS

| | | | |
|---|---|---|---|
| 3,113,066 | 12/1963 | Emond | 435/253 X |
| 3,911,110 | 10/1975 | Smirnoff | 424/93 |
| 3,937,813 | 2/1976 | Clark | 424/93 |
| 3,946,107 | 3/1976 | Westall | 424/93 |
| 4,000,258 | 12/1976 | Shieh et al. | 424/93 |
| 4,107,294 | 8/1978 | Chauthani | 424/93 |
| 4,277,564 | 7/1981 | Johnson | 435/253 X |
| 4,609,550 | 9/1986 | Fitz-James | 424/93 |
| 4,713,241 | 12/1987 | Wakisaka et al. | 424/93 |
| 4,797,279 | 1/1989 | Karamata et al. | 424/93 |

OTHER PUBLICATIONS

Can-Entomol. 118, 473–478 (1986), Morris.

*Primary Examiner*—Howard E. Schain
*Attorney, Agent, or Firm*—Alan A. Thomson

[57] ABSTRACT

An insecticidal composition for controlling or inhibiting the growth of larvae of the Bertha armyworm, comprising an insecticidal substance of one or more strains of *Bacillus thuringiensis* and an insecticidally acceptable carrier. The strains belong to the varieties aizawai, kurstaki and kenyae and include *Bacillus thuringiensis* var. aizawai strain HD-133.

9 Claims, No Drawings

TOXIC STRAINS OF THE BACTERIUM *BACILLUS THURINGIENSIS* FOR CONTROL OF THE BERTHA ARMYWORM *MAMESTRA CONFIGURATA*

This invention relates to a bacterial insecticide and a method for controlling or inhibiting the growth of larvae of *Mamestra configurata* (WALKER) (Lepidoptera, Noctuidae), commonly known as "the Bertha armyworm".

The Bertha armyworm (*Mamestra configurata*) is a lepidopterous insect and is a periodic economic pest of rapeseed, canola and several other cruciferous crops, as well as of some cereal crops. The larvae or caterpillars of this insect pest feed mainly on the leaves of plants. Infestations of the larvae on vegetation can be highly destructive to infested plants if not controlled.

The larvae of the Bertha armyworm, can be controlled, at present, by the use of highly toxic chemical insecticides. However, such chemical insecticides are potentially injurious not only to the natural agricultural environment (i.e. the plants it is intended to protect) but also to human beings and other animal life.

Bacterial based insecticides, which are environmentally more acceptable, have been suggested as an alternative to the use of chemical insecticides; see Canadian Patent Nos. 687428, 698579, 958330, 965001 and 1184137 as well as U.S. Pat. Nos. 3,113,066, 3,911,110, 3,937,813, 4,000,258 and 4,107,294. The above prior art generally discloses that *Bacillus thuringiensis* has a toxic quality which may be exploited in the form of bacterial based insecticides for lepidopterous insects; e.g. see U.S. Pat. Nos. 3,113,066 and 4,000,258.

A number of commercial insecticide formulations, based on *Bacillus thuringiensis*, are also known. In particular, commercial insecticides are known which are based on the exploitation of the toxic quality of *Bacillus thuringiensis* var. *kurstaki*; for example, products such as Dipel 132 (reg. TM) from Abbott Laboratories, North Chicago, Ill. and Thuricide 48 LV (reg. TM) from Zoecon, Palo Alto, Calif.

However, different strains of the various bacterial varieties of *Bacillus thuringiensis* have different toxic qualities. These differences can give rise to different effects on different insect species. Studies have shown that known commercial bacterial insecticides such as those referred to above are not sufficiently effective against larvae of the Bertha armyworm, *Mamestra configurata* (e.g. they are not economically competitive with other types of insecticides); MORRIS, O. N. 1986. Susceptibility of the bertha armyworm, *Mamestra configurata* (Lepidoptera, Noctuidae), to commercial formulations of *Bacillus thuringiensis* var. *kurstaki*. Can. Entomol. 118, 473–478.

The *Bacillus thuringiensis* strain, *Bacillus thuringiensis* var. *kurstaki* strain HD-1-S-1980 (referred to below), for example, does not have a sufficient toxic quality which can be used to effectively combat the Bertha armyworm, *Mamestra configurata*. The median lethal concentration of this strain has been found to be 964 µg primary powder/ml diet, the primary powder being a freeze dried product consisting essentially of the spores and the delta-endotoxin associated with this strain (see literature mentioned below). This median lethal concentration is equivalent to 15400 IU/ml diet; this relatively high value indicates that *Mamestra configurata* is one of the least susceptible noctuids to this HD-1 strain.

Efforts have been made to increase the effectiveness of bacterial insecticides based on *Bacillus thuringiensis* by associating the *Bacillus thuringiensis* with another insecticidally active substance; e.g. see Canadian Patent Nos. 687428, 698579, 965001 and 1184137 as well as U.S. Pat. Nos. 3,113,066, 3,911,110, 3,937,813, 4,000,258 and 4,107,294.

It would be advantageous to have bacterial insecticides based on one or more strains of *Bacillus thuringiensis* which have a toxic quality which can be exploited to effectively control the Bertha armyworm, *Mamestra configurata*.

It would, in particular, be advantageous to have bacterial insecticides wherein the active ingredient could be based, essentially only, on one or more strains of *Bacillus thuringiensis* which have a toxic quality which can be exploited to effectively control the larvae of the Bertha armyworm, *Mamestra configurata* i.e. against larvae in the growth stages thereof.

It would be advantageous to have bacterial insecticides which could be based on a combination (ie mixture) of the toxic quality of one or more strains of *Bacillus thuringiensis* and of one or more other active ingredients such as other insecticides or pesticides, the combination being effective against the Bertha armyworm, *Mamestra configurata*.

It would also be advantageous to have a method for combating infestations of the larvae of the Bertha armyworm, *Mamestra configurata* on crops or other plants by applying thereto one or more strains of *Bacillus thuringiensis* which have a toxic quality which can be exploited to effectively control the larvae of the Bertha armyworm, *Mamestra configurata*.

Accordingly, the present invention is concerned with the following strains of *Bacillus thuringiensis* which have shown themselves to have a toxic quality which may be exploited to provide an effective means of combating or controlling the larvae of the Bertha armyworm, *Mamestra configurata*, namely:

*Bacillus thuringiensis* var. *aizawai* strain HD-133;
*Bacillus thuringiensis* var. *aizawai* strain HD-131;
*Bacillus thuringiensis* var. *aizawai* strain HD-127;
*Bacillus thuringiensis* var. *aizawai* strain HD-113;
*Bacillus thuringiensis* var. *aizawai* strain HD-135;
*Bacillus thuringiensis* var. *kurstaki* strain HD-262;
*Bacillus thuringiensis* var. *kurstaki* strain HD-337; and
*Bacillus thuringiensis* var. *kenyae* strain HD-551.

The nomenclature of the *Bacillus thuringiensis* strains, as used herein, follows that used at the International Depository of *Bacillus thuringiensis* strains held by the U.S. Dept. of Agriculture, at the Subtropical Crop Insects Research Unit, Brownsville, Tex., U.S.A.; the strains are on deposit at this International Depository in Texas.

At the same time that the *Bacillus thuringiensis* strains, mentioned above, produce their respective spores, they also produce an associated delta-endotoxin (crystalline proteinous toxin). The delta-endotoxin of each of the above mentioned strains possess insecticidal activity against the Bertha armyworm. The spores and the associated delta-endotoxin produced in the cells of a particular strain can, if desired, be recovered therefrom in the form of a primary (i.e. freeze-dried) powder as described in the literature mentioned below.

Thus, the present invention, in particular, provides an insecticide composition for inhibiting the growth of larvae of *Mamestra configurata*, comprising
an insecticidal substance of a strain of

*Bacillus thuringiensis* and an insecticidally acceptable carrier said insecticidal substance comprising delta-endotoxin of said strain, said strain of *Bacillus thuringiensis* being selected from the class of strains consisting of

*Bacillus thuringiensis* var. *aizawai* strain HD-133;
*Bacillus thuringiensis* var. *aizawai* strain HD-131;
*Bacillus thuringiensis* var. *aizawai* strain HD-127;
*Bacillus thuringiensis* var. *aizawai* strain HD-113;
*Bacillus thuringiensis* var. *aizawai* strain HD-135;
*Bacillus thuringiensis* var. *kurstaki* strain HD-262;
*Bacillus thuringiensis* var. *kurstaki* strain HD-337; and
*Bacillus thuringiensis* var. *kenyae* strain HD-551.

In accordance with the present invention, the insecticide composition may comprise or include in addition to the insecticidal substance and the insecticidally acceptable carrier, a different insecticidally active substance; e.g. the carrier, instead of being inert, may itself have such activity.

The present invention also provides a method for controlling the growth of larvae of *Mamestra configurata* on a plant characterized in that a larvae growth-inhibiting amount of an insecticidal substance of a strain of *Bacillus thuringiensis* is applied to said plant, said insecticidal substance comprising delta-endotoxin of said strain, said strain of *Bacillus thuringiensis* being selected from the class of strains consisting of

*Bacillus thuringiensis* var. *aizawai* strain HD-133;
*Bacillus thuringiensis* var. *aizawai* strain HD-131;
*Bacillus thuringiensis* var. *aizawai* strain HD-127;
*Bacillus thuringiensis* var. *aizawai* strain HD-113;
*Bacillus thuringiensis* var. aizawai strain HD-135;
*Bacillus thuringiensis* var. *kurstaki* strain HD-262;
*Bacillus thuringiensis* var. *kurstaki* strain HD-337; and
*Bacillus thuringiensis* var. *kenyae* strain HD-551.

In accordance with the present invention, the insecticidal substance may comprise spores and delta-endotoxin of the *Bacillus thuringiensis* strain.

In accordance with the present invention, the insecticidal substance may be an insecticidal substance of two or more strains of *Bacillus thuringiensis* selected from the strains referred to above.

The following, strains of *Bacillus thuringiensis*, are preferred:

*Bacillus thuringiensis* var. *aizawai* strain HD-133;
*Bacillus thuringiensis* var. *aizawai* strain HD-131;
*Bacillus thuringiensis* var. *aizawai* strain HD-127; and
*Bacillus thuringiensis* var. *aizawai* strain HD-113.

The strain, *Bacillus thuringiensis* var. *aizawai* strain HD-133, is particularly preferred.

The insecticidal substance may be incorporated into the insecticide composition in any amount which will be effective for controlling the growth of larvae of *Mamestra configurata*.

The insecticidal quality of the above *Bacillus thuringiensis* strains (e.g. respective delta-endotoxin(s)) can be exploited by making use of an insecticidal substance which may comprise a culture broth of living cells, the cells containing spores and delta-endotoxin;

isolated living cells containing spores and delta-endotoxin;

isolated dead cells containing delta-endotoxin;

spores and delta-endotoxin recovered from cells; or delta-endotoxin recovered from cells and separated from the spores.

The insecticidal substance may take any other form which allows for the exploitation of the toxic quality of the *Bacillus thuringiensis* strain (e.g. of a respective delta-endotoxin). The insecticidal substance can thus be a fermented broth, a condensate, a freeze dried product . . . etc.

The insecticidal substance of a *Bacillus thuringiensis* strain described above may be applied to a plant (e.g. rapeseed, canola, cruciferous plants . . . etc.), in known manner in association with an inert liquid or solid carrier depending on whether the insecticidal substance is to be applied by means of a spraying or dusting technique. Any such application should of course be carried out so that those parts of the plant being eaten by the larvae will include the insecticidal substance, i.e. so that the insecticidal substance will be ingested by the larvae to facilitate the poisoning or infection thereof.

A liquid carrier or diluent such as water or a suitable oil may, for example, be used when it is desired to spray infested plants (e.g. leaves thereof), the insecticidal substance being dispersed or suspended in the liquid. The insecticidal substance may also be dispersed in an oil-in-water emulsion. The insecticide compositions may contain other compounds common in spray liquids, (e.g. suspending agents) but these should be selected on the basis that they will not effect the activity of the insecticidal substance.

A dry insecticide composition may also be applied to infested plants (e.g. leaves thereof) by dusting; for this purpose a dry form of the insecticidal substance may be admixed with a suitable inert powder such as talc, bentonite, diatomaceous earth, . . . etc.

Although insecticide compositions may be formulated using, essentially only, the insecticidal substance of a *Bacillus thuringiensis* strain as active ingredient, the insecticidal substance could also be used in conjunction with another different insecticidally active substance which exhibits its own insecticide activity or which may otherwise provide, in combination with the insecticidal substance, a composition with enhanced activity. Examples of bacterial based combinations are disclosed in Canadian Patent Nos. 687428, 965001 as well as in U.S. Pat. Nos. 3,113,066, 3,911,110, 3,937,813 4,000,258 and 4,107,294. These other substances should of course be chosen so as not to reduce or otherwise interfere with the effect of the insecticidal substance on the larvae of the Bertha armyworm, *Mamestra configurata*.

No matter what form the insecticide composition may take, the insecticidal substance of the *Bacillus thuringiensis* strains is applied to a plant and/or surrounding vegetation in an amount which will inhibit the growth of the larvae thereon i.e. in an amount which gives effective protection to the plant from larval predation.

The present invention is illustrated below with reference to the following examples and it is to be understood that the invention is not limited to the specific details thereof.

EXAMPLE NO. 1

Concentration-mortality Bioassays

The bioassays of this example were conducted on early third-instar larvae of *Mamestra configurata*.

For the purpose of the bioassays, a non-diapause population of larvae of *Mamestra configurata* was produced using the artificial diet and rearing technique as described by Bucher and Bracken, 1976; BUCHER, G.

E. and BRACKEN, G. L. 1976. The bertha armyworm, *Mamestra configurata* (Lepidoptera: Noctuidae). Artificial diet and rearing technique. *Can. Entomol.,* 108, 1327-38. Masses of 30 to 60 eggs that were three days old were placed in plastic ribbed creamer cups containing rearing diet and maintained in a light/dark cycle of 16:8 h, a temperature of about 25° C. and a relative humidity of about 60%. The eggs hatched the next day. The larvae moulted to the third instar four days later and were thereafter used for the bioassays.

The *Bacillus thuringiensis* strains used in the bioassays including the reference standard strain are set out in TABLE 1 below.

TABLE 1

| Strain Reference Number (SRN) | Corresponding *Bacillus thuringiensis* Strain |
|---|---|
| 1. | *Bacillus thuringiensis* var. *aizawai* strain HD-133 |
| 2. | *Bacillus thuringiensis* var. *aizawai* strain HD-131 |
| 3. | *Bacillus thuringiensis* var. *aizawai* strain HD-127 |
| 4. | *Bacillus thuringiensis* var. *aizawai* strain HD-113 |
| 5. | *Bacillus thuringiensis* var. *kurstaki* strain HD-262 |
| 6. | *Bacillus thuringiensis* var. *aizawai* strain HD-135 |
| 7. | *Bacillus thuringiensis* var. *kenyae* strain HD-551 |
| 8. | *Bacillus thuringiensis* var. *kurstaki* strain HD-337 |
| reference standard | *Bacillus thuringiensis* var. *kurstaki* strain HD-1-S-1980 |

Primary powders of all of the *Bacillus thuringiensis* strains referred to in TABLE 1, including the reference standard strain, *Bacillus thuringiensis* var. *kurstaki* strain HD-1-S-1980, were obtained from the International Depository of *Bacillus thuringiensis* strains maintained by H. T. Dulmage (i.e. held by the U.S. Dept. of Agriculture, at the Subtropical Crop Insects Research Unit, Brownsville, Tex., U.S.A.). The primary powders were freeze dried products consisting essentially of spores and delta-endotoxin of each of the respective strains. All of the strains, as obtained, had been previously fermented and recovered as described by Dulmage et al. (1981) infra and were stored at 4° C. in sealed vials; DULMAGE, H. T., and COOPERATORS. 1981. Insecticidal activity of isolates of *Bacillus thuringiensis* and their potential for pest control. In "Microbial Control of Pests and Plant Diseases, 1970–1980" (H. D. Burges, ed.), pp. 193–222. Academic press, New York.

The bioassay procedures proposed by Dulmage et al (1981) supra, were used. The artificial diet used in the bioassays was the rearing diet of Bucher and Bracken, 1976 supra, except that the antibiotic, chlorotetracycline hydrochloride, was omitted, since it may affect the response of the larvae.

At the beginning of a bioassay a specified or required weight of the primary powder of a strain to be tested and of the standard reference strain were each resuspended in a respective buffered saline solution (as per Dulmage et al 1981 supra). These *Bacillus thuringiensis* samples were then homogenized with a probe sonicator (60 watts) for 1 minute. A wetting agent, Tween 80, was added at a rate of one tenth of a mol of a 1% solution per 10 ml of sample. Samples for control treatments received only the sample volume of buffered saline solution and wetting agent. The samples were then incorporated into a liquid bioassay diet at a sample to total volume ratio of 1:10 and mixed in a blender at high speed for 4 minutes. The diet was then poured into plastic creamer cups (ca. 5 ml/cup) and allowed to set. One early third instar larvae was placed in each diet cup which was then sealed with a cardboard lid and inverted onto a rearing board. The cups were placed in an incubator at 25° C., 60% humidity, and a light/dark cycle of 16:8 h, where the larvae fed ad libitum for seven (7) days.

The *Bacillus thuringiensis* strains referred to in TABLE 1 were bioassayed as above to reveal concentration-mortality response with concurrent bioassays of the reference standard strain also referred to in TABLE 1. The median lethal concentrations, $LC_{50}$ (μg of primary powder/ml of diet), were determined by adoption of the procedure proposed by Robertson et al., 1984; ROBERTSON, J. L., SMITH, K. C., SAVIN, N. E., and LAVIGNE, R. J. 1984. Effects of dose selection and sample size on the precision of lethal dose estimates in dose-mortality regression. *J. Econ. Entomol.*, 77, 833–837. The larvae were thus divided into a number of groups, each group consisting of thirty (30) larvae. A separate group of thirty (30) larvae was exposed to each of a number of different concentrations of a *Bacillus thuringiensis* strain to be tested as well as of the reference standard strain. Five groups of thirty (30) larvae were also exposed to control treatments for each bioassay.

The median lethal concentration $LC_{50}$ and 95% confidence interval were determined from regressions of probit mortality after seven (7) days against log concentration. Relative potency and the 95% confidence interval for each bioassay of a tested *Bacillus thuringiensis* strain was calculated from a parallel line regression with the concurrent bioassay of the standard reference strain; FINNEY, D. J. 1971 "Probit Analysis". Cambridge University Press, London.

The results of the concentration mortality response bioassays are summarized in TABLE 2 below with the *Bacillus thuringiensis* strains being ranked in order of relative potency.

TABLE 2

| | | Test Strain | | Reference Stndrd Strain | | Parallel line Probit Analysis | |
|---|---|---|---|---|---|---|---|
| SRN | n | $LC_{50}$ (& CI) | Slope ± (SEb) | $LC_{50}$ (& CI) | Slope ± (SEb) | Rel. pot. (& CI) | Slope ± (SEb) |
| 1. | 360 | 334 (242–405) | 4.61 (0.964) | 1700 (1270–5360) | 2.60 (0.946) | 5.15 (nsr) | 3.15 |
| 2. | 390 | 398 (297–493) | 3.21 (0.581) | 1240 (1050–1450) | 4.16 (0.716) | 3.05 (2.93–3.99) | 3.55 (0.448) |
| 4. | 390 | 356 (220–473) | 2.17 (0.500) | 1110 (884–1350) | 3.72 (0.775) | 2.88 (nsr) | 2.69 |
| 3. | 390 | 390 (271–487) | 3.27 (0.795) | 1136 (951–1377) | 4.41 (0.875) | 2.86 (2.23–3.85) | 3.77 (0.588) |

TABLE 2-continued

| SRN | Test Strain n | Test Strain LC$_{50}$ (& CI) | Test Strain Slope ± (SEb) | Reference Stndrd Strain LC$_{50}$ (& CI) | Reference Stndrd Strain Slope ± (SEb) | Parallel line Probit Analysis Rel. pot. (& CI) | Parallel line Probit Analysis Slope ± (SEb) |
|---|---|---|---|---|---|---|---|
| 7. | 570 | 432 (357–567) | 3.42 (0.869) | 1180 (nsr) | 1.62 | 2.59 (nsr) | 2.46 |
| 6. | 390 | 481 (295–613) | 3.42 (0.896) | 1250 (1090–1470) | 4.82 (0.814) | 2.54 (nsr) | 3.98 |
| 5. | 390 | 431 (330–516) | 3.52 (0.618) | 1110 (980–1270) | 5.25 (0.803) | 2.50 (nsr) | 4.15 |
| 8. | 390 | 543 (260–780) | 2.45 (0.818) | 1220 (1140–1300) | 5.70 (0.550) | 2.19 (nsr) | 3.39 |

NOTES:
Reference Stndrd Strain = *Bacillus thuringiensis* var. *kurstaki* strain HD-1-S-1980;
SRN = Strain Reference Number from TABLE 1;
n = number of larvae of the Bertha armyworm treated;
LC$_{50}$ = Dose (μg of primary powder of test strain/ml of diet) causing 50% mortality;
CI = 95% confidence interval;
Slope = slope of probit regression line;
SEb = standard error of slope;
rel. pot. = relative potency; and
nsr = non-significant regression.

As can be seen from TABLE 2, the *Bacillus thuringiensis* strains of the present invention (i.e. those having strain reference numbers 1. to 8. in TABLE 1) are more toxic after seven (7) days than the standard reference strain. The most potent strains overall are
*Bacillus thuringiensis* var. *aizawai* strain HD-133;
*Bacillus thuringiensis* var. *aizawai* strain HD-131;
*Bacillus thuringiensis* var. *aizawai* strain HD-127; and
*Bacillus thuringiensis* var. *aizawai* strain HD-113;
the *Bacillus thuringiensis* var. *aizawai* strain HD-133 being the most potent of all. These latter *Bacillus thuringiensis* strains are all in the order of two (2) to more than five (5) times more potent than the standard reference strain. At a concentration of 500 μg of primary powder/ml of diet these latter *Bacillus thuringiensis* strains were more toxic than the standard reference strain after both four (4) and seven (7) days.

EXAMPLE NO. 2

Relative Toxicity Bioassays of other strains with respect to the standard reference strain, *Bacillus thuringiensis* var. *kurstaki* strain HD-1-S-1980.

A number of bioassays were conducted using generally the same technique as outlined in example 1, i.e. third instar larvae used . . . etc. As can be seen from TABLE 3 below, the three *Bacillus thuringiensis* strains referred to therein, have a toxic quality toward the Bertha armyworm, which is even lower than that of the standard reference strain (HD-1-S-1980).

TABLE 3

| *Bacillus thuringiensis* Strain | n | Mortality (%) | Relative Toxicity |
|---|---|---|---|
| var. *kenyae* strain HD-123 | 100 | 2.00 | −13.1 |
| var. *aizawai* strain HD-629 | 100 | −4.17 | −15.6 |
| var. *kurstaki* strain HD-255 | 100 | 3.00 | −29.1 |

NOTES:
n = number of larvae of the Bertha armyworm treated;
Mortality = Mortality (%) of larvae feeding for seven (7) days on diet containing a concentration of 500 μg primary powder/ml diet of the respective strains; Mortalities were corrected for natural response; and
Relative Toxicity = Test for independence of mortalities between treatments of each strain and that of the standard reference strain (HD-S-1980); Chi-square values less than −3.84 indicate toxicities significantly lower that that of the standard reference strain (HD-S-1980).

The embodiments of the invention in which an exclusive property or privilege is claimed are defined as follows:

1. A method for killing the larvae of *Mamestra configurata* on a plant characterized in that a larvicidal amount of an insecticidal substance of at least one selected strain of *Bacillus thuringiensis* is applied to said plant,
said insecticidal substance comprising delta-endotoxin of said strain,
said strain of *Bacillus thuringiensis* being selected from the class of strains consisting of
*Bacillus thuringiensis* var. *aizawai* strain HD-133;
*Bacillus thuringiensis* var. *aizawai* strain HD-131;
*Bacillus thuringiensis* var. *aizawai* strain HD-127;
*Bacillus thuringiensis* var. *aizawai* strain HD-113;
*Bacillus thuringiensis* var. *aizawai* strain HD-135;
*Bacillus thuringiensis* var. *kurstaki* strain HD-262;
*Bacillus thuringiensis* var. *kurstaki* strain HD-337; and
*Bacillus thuringiensis* var. *kenyae* strain HD-551.

2. A method as defined in claim 1 wherein said strain of *Bacillus thuringiensis* is selected from the class of strains consisting of
*Bacillus thuringiensis* var. *aizawai* strain HD-133;
*Bacillus thuringiensis* var. *aizawai* strain HD-131;
*Bacillus thuringiensis* var. *aizawai* strain HD-127; and
*Bacillus thuringiensis* var. *aizawai* strain HD-113.

3. A method as defined in claim 1 wherein wherein said insecticidal substance is an insecticidal substance of *Bacillus thuringiensis* var. *aizawai* strain HD-133.

4. A method as defined in claim 1 wherein said insecticidal substance comprises spores and delta-endotoxin of said strain.

5. A method as defined in claim 2 wherein said insecticidal substance comprises spores and delta-endotoxin of said strain.

6. A method as defined in claim 3 wherein said insecticidal substance comprises spores and delta-endotoxin of said strain.

7. A Method as defined in claim 1 wherein said insecticidal substance is an insecticidal substance of two or more strains of *Bacillus thuringiensis* selected from said class of strains.

8. A method as defined in claim 2 wherein said insecticidal substance is an insecticidal substance of two or more strains of *Bacillus thuringiensis* selected from said class of strains.

9. A method as defined in claim 1 wherein the plant is a member of the group of plants consisting of rapeseed, canola and cruciferous plants.

* * * * *